United States Patent [19]
Wheeler

[11] 3,933,808
[45] Jan. 20, 1976

[54] CEPHALOSPORIN ESTERS

[75] Inventor: William J. Wheeler, Indianapolis, Ind.

[73] Assignee: Eli Lilly and Company, Indianapolis, Ind.

[22] Filed: May 20, 1974

[21] Appl. No.: 471,528

[52] U.S. Cl............................. 260/243 C; 424/246
[51] Int. Cl.² ........................................ C07D 501/20
[58] Field of Search .............................. 260/243 C

[56] References Cited
UNITED STATES PATENTS 3,697,507  10/1972  Frederiksen et al. .......... 260/243 C
3,840,531  10/1974  Greene........................... 260/243 C

*Primary Examiner*—Nicholas S. Rizzo
*Attorney, Agent, or Firm*—Charles W. Ashbrook; Walter E. Buting; Everet F. Smith

[57] ABSTRACT

Acyloxymethyl esters of 7-D-mandelamido-3-(1-methyl-1,2,3,4-tetrazole-5-thiomethyl)-3-cephem-4-carboxylic acid are orally active broad spectrum antibiotics.

7 Claims, No Drawings

CEPHALOSPORIN ESTERS

BACKGROUND OF THE INVENTION

Numerous drugs are now known and currently in use that are not absorbed at all, or are absorbed only poorly, from the gastrointestinal tract. In particular, many important semisynthetic cephalosporin antibiotics that are now available and are routinely used must be administered parenterally. Cephalothin Sodium, for example, is administered intramuscularly or intravenously, thus requiring a trained medical person to treat the patient. It has long been an objective of research to provide potent drugs that are orally active, especially in the field of cephalosporin and penicillin antibiotics. Jansen and Russell prepared several acyloxymethyl esters of various penicillins and found that some of the esters were orally active; U.S. Pat. No. 3,250,679. At the same time, however, Jansen and Russell reported that of the many closely related acyloxymethyl esters which were prepared and tested, only the acetoxymethyl ester of benzylpenicillin displayed oral absorption to a significant extent. In fact, some acyloxymethyl esters of certain penicillins showed no oral absorption at all, for example the acetoxymethyl ester of Cloxacillin.

It is an object of this invention to provide acyloxymethyl esters of particularly potent cephalosporin antibiotics, which esters are substantially totally absorbed orally, whereas the parent cephalosporin acids from which they are derived are essentially completely unabsorbed. It is a further object of the present invention to provide esters having additional desirable qualities, such as crystallinity and extended stability for example, which the parent cephalosporin acids normally do not possess.

SUMMARY OF THE INVENTION

This invention relates to new acyloxymethyl esters of 7-D-mandelamido derivatives of 7-amino-3-(1-methyl-1,2,3,4-tetrazole-5-thiomethyl)-3-cephem-4-carboxylic acid, which esters are potent antibacterial agents and are orally absorbed into the gastrointestinal tract. In particular, the invention provides acyloxymethyl esters having the formula

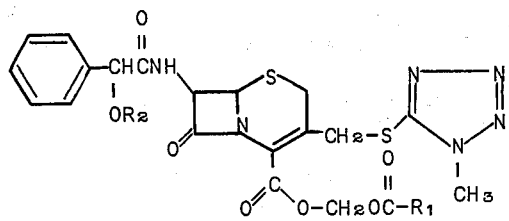

in which $R_1$ is lower alkyl and $R_2$ is hydrogen or lower alkanoyl. The compounds disclosed herein are prepared by reaction of the corresponding cephalosporin acid with a halomethyl ester of a lower alkanoic acid. The new cephalosporin esters are useful as oral antibiotics.

DETAILED DESCRIPTION OF THE INVENTION

As hereinbefore indicated, the compounds of this invention have the formula

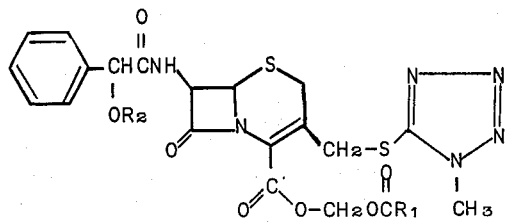

I $R_1$ in the foregoing formula is a straight or branched chain $C_1$–$C_4$ alkyl group, typical examples being methyl, ethyl, isopropyl and tert-butyl.

$R_2$ in the formula represents hydrogen or a $C_1$–$C_4$ alkanoyl group such as formyl, acetyl, isobutyryl, and the like. Preferred lower alkanoyl groups are formyl and acetyl, the formyl group being especially preferred.

The most preferred compounds of this invention are those in which $R_1$ is methyl or tert-butyl, and $R_2$ is hydrogen or formyl.

As indicated hereinbefore, the compounds of this invention can be prepared by reacting a cephalosporin acid such as, for example, 7-D-mandelamido-3-(1-methyl-1,2,3,4-tetrazole-5-thiomethyl)-3-cephem-4-carboxylic acid, with a halomethyl ester of a lower alkanoic acid. Halo as used herein refers to chloro, bromo, or iodo. Typical examples of halomethyl esters of lower alkanoic acids useful in preparing the compounds of this invention are: chloromethyl acetate, bromomethyl acetate, bromomethyl n-propionate, iodomethyl n-butanoate, bromomethyl pivalate, chloromethyl pivalate, and the like. Preferred halomethyl esters of lower alkanoic acids are chloromethyl acetate, bromomethyl acetate, chloromethyl pivalate, and bromomethyl pivalate.

The esterification reaction is preferably carried out in an unreactive organic solvent and in the presence of a suitable base. Suitable unreactive solvents include amides, nitriles, halogenated hydrocarbons, sulfoxides, ethers, ketones, and the like. Examples of unreactive solvents include N-dimethylformamide, N,N-dimethylacetamide, dichloromethane, chloroform, dimethyl sulfoxide, acetonitrile, diethyl ether, dioxane, tetrahydrofuran, acetone, methyl ethyl ketone, and the like. The particular solvent selected is not critical. Preferred solvents include N,N-dimethylformamide, acetone, and acetonitrile.

A base is normally employed in the esterification reaction to act as an acid binding agent. The particular base employed is not critical, and can be either organic or inorganic. Suitable bases include organic amines such as triethylamine, dicyclohexylamine, N-methylmorpholine, pyridine, N,N-diethyl-aniline, and the like, as well as inorganic bases such a sodium bicarbonate, lithium carbonate, magnesium hydroxide, and like bases. Preferred bases used in preparing the compounds of this invention are triethylamine, dicyclohexylamine and pyridine. The amount of base used in the esterification reaction is normally about an equimolar amount relative to the starting cephalosporin acid;

however more or less base can be used, if desired. Generally, large excesses of base are avoided, since excess base often promotes isomerization of the double bond in the thiazolidine ring system. More specifically, the amount of base in the reaction mixture at any one time is preferably maintained at a minimum. This can generally be accomplished by adding the base to the reaction mixture at a relatively slow rate.

The cephalosporin acid and the halomethyl ester of the alkanoic acid are preferably combined in equimolar amounts. An excess of either reagent can be used, however, if desired. The reaction is generally carried out at a temperature below about 50°C., preferably at 20° to 30°C. The reaction is substantially complete after about 2 to about 24 hours. For best results, the reaction is allowed to continue for about 4 to 14 hours. The product can be isolated by adding the reaction mixture to a suitable water immiscible organic solvent, such as ethyl acetate or chloroform for example, and washing the solution with water. If excess carboxylic acid is used in the reaction, the organic solution can be washed with a dilute base, for example dilute aqueous sodium hydroxide or sodium bicarbonate, thereby washing out unreacted acid. The product is generally recovered as a solid and can be further purified, if desired, by standard methods such as crystallization or chromatography.

The cephalosporin carboxylic acids which are required as starting materials in the present invention can be prepared according to any of a variety of methods, such as those described in detail in U.S. Pat. No. 3,641,021. The halomethyl esters of lower alkanoic acids are readily available compounds, or alternatively can be prepared by well established methods.

The following compounds are illustrative of the lower acyloxymethyl esters provided by the present invention.

Acetoxymethyl 7-D-mandelamido-3-(1-methyl-1,2,3,4-tetrazole-5-thiomethyl)-3-cephem-4-carboxylate;

Propionyloxymethyl 7-D-mandelamido-3-(1-methyl-1,2,3,4-tetrazole-5-thiomethyl)-3-cephem-4-carboxylate;

Pivaloyloxymethyl 7-[D-(O-formyl)mandelamido]-3-(1-methyl-1,2,3,4-tetrazole-5-thiomethyl)-3-cephem-4-carboxylate;

Butyryloxymethyl 7-[D-(O-acetyl)mandelamido]-3-(1-methyl-1,2,3,4-tetrazole-5-thiomethyl)-3-cephem-4-carboxylate;

Pivaloyloxymethyl 7-[D-(O-butyryl)mandelamido]-3-(1-methyl-1,2,3,4-tetrazole-5-thiomethyl)-3-cephem-4-carboxylate;

Acetoxymethyl 7-[D-(O-formyl)mandelamido]-3-(1-methyl-1,2,3,4-tetrazole-5-thiomethyl)-3-cephem-4-carboxylate;

Pivaloyloxymethyl 7-D-mandelamido-3-(1-methyl-1,2,3,4-tetrazole-5-thiomethyl)-3-cephem-4-carboxylate; and the like.

The compounds provided by this invention are new chemical compounds that are useful pharmacological agents, especially as antibacterial agents and most especially as orally effective antibacterial agents. They are active against a broad spectrum of Gram positive and Gram negative organisms such as *Staphylococcus aureus*, *Salmonella heidelberg*, *Streptococcus pyogenes*, *Escherichia coli*, as well as others. These compounds display exceptionally high blood levels after oral administration. For example, the acetoxymethyl ester of 7-D-mandelamido-3-(1-methyl-1,2,3,4-tetrazole-5-thiomethyl)-3-cephem-4-carboxylic acid has displayed as much as a 73 fold increase in blood levels over those observed with the parent free acid following oral administration.

The compounds of the invention can be administered in single or multiple dosage units, and are most preferably administered orally, either alone or with a suitable carrier or diluent. Typical pharmaceutical diluents or carriers include lactose, sucrose, starch powder, cellulose, calcium sulfate, gelatin, and the like. Such compositions can be formulated as tablets or enclosed in capsules for convenient administration. The compounds can also be mixed with a liquid and administered as elixirs, suspensions, and the like.

The following detailed examples further illustrate the invention and are not intended to limit the scope thereof.

The abbreviations used in the examples refer to the following:

nmr — nuclear magnetic resonance spectrum
$CDCl_3$ — deuterated chloroform
$\delta$ — delta value
s — singlet
d — doublet
DMF — N,N-dimethylformamide

EXAMPLE 1

Pivaloyloxymethyl 7-D-mandelamido-3-(1-methyl-1,2,3,4-tetrazole-5-thiomethyl)-3-cephem-4-carboxylate.

To a solution of 4.62 g. of 7-D-mandelamido-3-(1-methyl-1,2,3,4-tetrazole-5-thiomethyl)-3-cephem-4-carboxylic acid and 1.53 g. of chloromethyl pivalate in 25 cc. of DMF was added dropwise a solution of 1.81 g. of dicyclohexylamine in 15 cc. of DMF. The reaction mixture was stirred at room temperature for about fifteen minutes, after which time 1.03 g. of sodium bromide was added. The reaction mixture was stirred for twelve hours at room temperature. After the reaction mixture was filtered, the filtrate was added to 700 cc. of ethyl acetate. The organic solution was washed successively with aqueous saturated sodium chloride solution, aqueous sodium bicarbonate solution, 1 N hydrochloric acid, and water. After the organic solution was dried, the solvent was removed under reduced pressure to provide 1.6 g. of crystalline residue. The residue was recrystallized from fresh ethyl acetate to afford pivaloyloxymethyl 7-D-mandelamido-3-(1-methyl-1,2,3,4-tetrazole-5-thiomethyl)-3-cephem-4-carboxylate. M.P. 174°–176°C.

Analysis — Calc. for $C_{24}H_{28}N_6O_7S_2$ (percent): C, 49.99; H, 4.89; N, 14.57. Found (percent): C, 49.72; H, 4.83; N, 14.37.

nmr $(CDCl_3)$: $\delta$ 1.15 (s, 9H, —C(CH$_3$)$_3$); $\delta$ 3.7 (d, 2H, C—2H); $\delta$ 3.95 (s, 3H, N—CH$_3$); $\delta$ 8.70–8.75 (d, 1H, N—H).

EXAMPLE 2

Acetoxymethyl 7-D-mandelamido-3-(1-methyl-1,2,3,4tetrazole-5-thiomethyl)-3-cephem-4-carboxylate.

A solution of 0.595 cc. of triethylamine in 10 cc. of acetone was added dropwise to a stirred solution of 2.0 g. of 7-D-mandelamido-3-(1-methyl-1,2,3,4-tetrazole-5-thiomethyl)-3-cephem-4-carboxylic acid and 1.72 cc. of bromomethyl acetate in 10 cc. of DMF. The reaction mixture was stirred at room temperature for two hours. The reaction mixture was filtered and the filtrate was added to 300 cc. of chloroform, washed with water and with aqueous sodium bicarbonate, and dried. The solvent was removed under reduced pressure, affording a white foam. The crude product was crystallized from methyl alcohol, providing acetoxymethyl 7-D-mandelamido-3-(1-methyl-1,2,3,4-tetrazole-5-thiomethyl)-3-cephem-4-carboxylate as white crystals. M.P. 126°–130°C. dec.

| | |
|---|---|
| Analysis — Calc. for $C_{21}H_{22}N_6O_7S_2$ (percent): | |
| | C, 47.18; H, 4.15; N, 15.72; S, 12.00. |
| Found (percent): | C, 47.03; H, 4.11; N, 15.45; S, 12.05. |
| nmr (CDCl$_3$): | $\delta$ 2.05 (s, 3H, $\overset{O}{\overset{\|}{C}}$—CH$_3$) |
| | $\delta$ 3.6 (s, 2H, C—2H) |
| | $\delta$ 3.82 (s, 3H, N—CH$_3$) |
| | $\delta$ 8.05 (d, 1H, N—H). |

I claim:
1. The compound of the formula

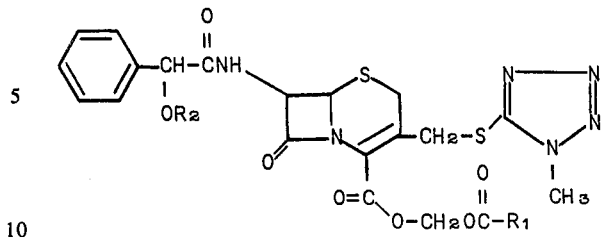

wherein:
$R_1$ is $C_1$–$C_4$ alkyl;
$R_2$ is hydrogen or $C_1$–$C_4$ alkanoyl.
2. The compound of claim 1, wherein $R_1$ is methyl.
3. The compound of claim 2, wherein $R_2$ is hydrogen.
4. The compound of claim 2, wherein $R_2$ is formyl.
5. The compound of claim 1, wherein $R_1$ is tert-butyl.
6. The compound of claim 5, wherein $R_2$ is hydrogen.
7. The compound of claim 5, wherein $R_2$ is formyl.

* * * * *